US008663704B2

(12) United States Patent
Minatelli et al.

(10) Patent No.: US 8,663,704 B2
(45) Date of Patent: Mar. 4, 2014

(54) COMPOSITION AND METHOD TO IMPROVE BLOOD LIPID PROFILES AND OPTIONALLY REDUCE LOW DENSITY LIPOPROTEIN (LDL) PER-OXIDATION IN HUMANS

(75) Inventors: John A. Minatelli, Mt. Dora, FL (US); W. Stephen Hill, Ocala, FL (US); Rudi E. Moerck, Sanford, FL (US)

(73) Assignee: U.S. Nutraceuticals, LLC, Eustis, FL (US)

(*) Notice: Subject to any disclaimer, the term of this patent is extended or adjusted under 35 U.S.C. 154(b) by 159 days.

(21) Appl. No.: 13/093,201

(22) Filed: Apr. 25, 2011

(65) Prior Publication Data
US 2011/0268811 A1    Nov. 3, 2011

Related U.S. Application Data

(60) Provisional application No. 61/329,744, filed on Apr. 30, 2010.

(51) Int. Cl.
*A61K 31/202* (2006.01)
*A61K 31/05* (2006.01)
*A61K 35/56* (2006.01)

(52) U.S. Cl.
CPC ............. *A61K 31/202* (2013.01); *A61K 31/05* (2013.01); *A61K 35/612* (2013.01); *A61K 2300/00* (2013.01)
USPC .......................................... 424/523; 424/538

(58) Field of Classification Search
None
See application file for complete search history.

(56) References Cited

U.S. PATENT DOCUMENTS

2007/0098808 A1    5/2007   Sampalis ...................... 424/523
2011/0160161 A1*   6/2011   Sampalis et al. ................ 514/78

OTHER PUBLICATIONS

Deutsch, L. "Evaluation of the effect of Neptune Krill Oil on chronic inflammation and arthritic symptoms", J Am Coll Nutr. 2007, vol. 26, pp. 39-48.*
Longvah T, Deosthale YG, and Kumar PU, "Nutritional and short term toxicological evaluation of Perilla seed oil", Food Chemistry 2000, vol. 70, pp. 13-16.*
Hjaltason B, and Haraldsson GG, "Fish Oils and Lipids from Marine Sources" In: Modifying Lipids for Use in Food. Gunstone F.D., Ed.; Woodhead Publishing: Cambridge, 2006; pp. 57-79.*
Harris, "*Fish Oils and Plasma Lipid and Lipoprotein Metabolism in Humans: A Critical Review*," Journal of Lipid Research, vol. 30, No. 6, 1989, pp. 785-807.
Bunea et al., "*Evaluation of the Effects of Neptune Krill Oil on the Clinical Course of Hyperlipidemia*," Alternative Medicine Review, vol. 9, No. 4, 2004, pp. 420-428.

Tou et al., "*Krill for Human Consumption: Nutritional Value and Potential Health Benefits*," Nutrition Reviews, vol. 65, No. 2, Feb. 2007, pp. 63-77.
Anonymous, "*Krill Oil Cholesterol Study Brings Breakthrough Results*," Dec. 23, 2008, Retrieved from the Internet: http://web.archive.org/web/20081223105203/http://www.krill-oil-benefits.com/krill-oil-cholesterol.php, 3 pages.
Anonymous, "*Astaxanthin: The Super Antioxidant that Makes Neptune Krill Oil the Disease-Fighting, Inflammation-Fighting, PMS-Relieving, Anti-Aging Wonder Supplement for Every Body*," Sep. 21, 2008, Retrieved from the Internet: http://web.arhive.org/web/20080921180826/http://www.krill-oil-benefits.com/astaxanthin.php, 2 pages.
Anonymous, "*Antioxidants: The "Free Radical Scavengers" Believed to Slow the Aging Clock and Protect Against Many Health Problems*," Dec. 5, 2008, Retrieved from the Internet: http://web.archive.orq/web/20081205014602/http://www.krill-oil-benefits.com/antioxidants.php, 2 pages.
Mason et al., "Rofecoxib Increases Susceptibility of Human LDL and Membrane Lipids to Oxidative Damage: A Mechanism of Cardiotoxicity," Cardiovasc Pharmacol, vol. 47, Supplement 1, 2006, pp. S7-S14.
Kidd, "Astaxanthin, Cell Membrane Nutrient With Diverse Clinical Benefits and Anti-Aging Potential," Alternative Medicine Review, vol. 16, No. 4, pp. 355-364.
Nakagawa et al., "Antioxidant Effect of Astaxanthin on Phospholipid Peroxidation in Human Erythrocytes," British Journal of Nutrition (2011), Nov. 26, 2010, pp. 1-9.
Fassett et al., "Astaxanthin vs. Placebo on Arterial Stiffness, Oxidative Stress and Inflammation in Renal Transplant Patients (Xanthin): A Randomised Controlled Trial," BMC Nephrology, Dec. 18, 2008, pp. 1-8.
Mercola, "Astaxanthin for Heart Health and Chronic Pain," Downloaded from the Internet on Dec. 4, 2013 at www.mercola.com, Sep. 12, 2012, pp. 1-6.
Maoka et al., "Stereochemical Investigation of Carotenoids in the Antarctic Krill Euphausia Superba," Bulletin of the Japanese Society of Scientific Fisheries, Mar. 14, 1985, pp. 1671-1673.
Breithaupt, "Identification and Quantification of Astaxanthin Esters in Shrimp (*Pandalus borealis*) and in a Microalga (*Haematococcus pluvialis*) by Liquid Chromatography-Mass Spectrometry Using Negative Ion Atmospheric Pressure Chemical Ionization," Institut fur Lebensmittelchemie, Universitat Hohenheim, Germany, Apr. 14, 2004, pp. 1-6.
Yamaguchi et al., "Supercritical Carbon Dioxide Extraction of Oils from Antarctic Krill," J. Agric. Food Chem., vol. 34, No. 5, American Chemistry Society, 1986, pp. 904-907.

* cited by examiner

*Primary Examiner* — Allison Ford
*Assistant Examiner* — Michelle F Paguio Frising
(74) *Attorney, Agent, or Firm* — Allen, Dyer, Doppelt, Milbrath & Gilchrist, P.A.

(57) ABSTRACT

A composition and method which improves blood lipid profiles and optionally reduces low density lipoprotein (LDL) per-oxidation in humans by administering a therapeutic amount of a composition comprising krill oil in combination with astaxanthin or a mixture of fish oil derived, choline based, phospholipid bound omega-3 fatty acid mixture including phospholipid bound polyunsaturated EPA and DHA. In one embodiment, the krill oil is derived from *Euphasia* spp., comprising Eicosapentaenoic (EPA) and Docosahexaenoic (DHA) fatty acids in the form of triacylglycerides and phospholipids. The krill oil includes at least 10% EPA and 5% DHA, of which greater than 50% are in the form of phospholipids and the 1-4000 mg of krill oil per daily dose is delivered.

7 Claims, No Drawings

US 8,663,704 B2

COMPOSITION AND METHOD TO IMPROVE BLOOD LIPID PROFILES AND OPTIONALLY REDUCE LOW DENSITY LIPOPROTEIN (LDL) PER-OXIDATION IN HUMANS

RELATED APPLICATION(S)

This application is based upon prior filed provisional application Ser. No. 61/329,744, filed Apr. 30, 2010; and related to prior filed U.S. patent applications Ser. No. 12/840,372, filed Jul. 21, 2010, and Ser. No. 13/079,238, filed Apr. 4, 2011, the disclosures which are hereby incorporated by reference in their entirety.

FIELD OF THE INVENTION

This invention relates to improving blood lipid profiles and reducing low density lipoprotein (LDL) oxidation using therapeutic compositions and methods derived from krill oil extracts and/or marine oil compositions. This invention also relates to improving blood lipid profiles and reducing LDL using therapeutic composition and methods derived from a mixture of fish oil and fish oil derived, choline based, phospholipid bound fatty acids including polyunsaturated EPA and DHA either alone or mixed with synergistic additives.

BACKGROUND OF THE INVENTION

The use of krill and/or marine oil are disclosed in U.S. Patent Publication Nos. 2004/0234587; 2004/0241249; and 2007/0098808, the disclosures which are hereby incorporated by reference in their entirety, and discussed in related U.S. patent application Ser. Nos. 12/840,372 and 13/079,238. The beneficial aspects of using krill and/or marine oil are shown also in a research paper published by L. Deutsch as "Evaluation of the Effect of Neptune Krill Oil on Chronic Inflammation and Arthritic Symptoms," published in the Journal of the American College of Nutrition, Volume 26, No. 1, 39-49 (2007), the disclosure which is hereby incorporated by reference in its entirety.

The published '587, '249 and '808 applications discuss the beneficial aspects of using krill oil in association with pharmaceutically acceptable carriers. As an example, this krill and/or marine oil can be obtained by the combination of detailed steps as taught in the '808 application, by placing krill and/or marine material in a ketone solvent, separating the liquid and solid contents, recovering a first lipid rich fraction from the liquid contents by evaporation, placing the solid contents and organic solvent in an organic solvent of the type as taught in the specification, separating the liquid and solid contents, recovering a second lipid rich fraction by evaporation of the solvent from the liquid contents and recovering the solid contents. The resultant krill oil extract has also been used in an attempt to decrease lipid profiles in patients with hyperlipidemia. The '808 publication gives details regarding this krill oil as derived using those general steps identified above.

The published article gives further details of how the processed krill oil alone, at 3000 mgs/daily dose is a product that aids in treating chronic inflammation and arthritic symptoms. The article describes a study, which had several objectives: a) to evaluate the effect of NEPTUNE KRILL OIL on C-reactive protein (C-RP) on patients with chronic inflammation; and b) to evaluate the effectiveness of the NEPTUNE KRILL OIL on arthritic symptoms. The method used a randomized, double blind, placebo controlled study protocol. Ninety patients were recruited with either a confirmed diagnosis of cardiovascular disease and/or rheumatoid arthritis and/or osteoarthritis and with increased levels of CRP (>1.0 mg/dl) upon three consecutive weekly blood analysis prior to initiation of oral treatment with krill oil. It is important to note that C-RP is a well known biomarker for risk of cardiovascular disease, therefore in this trial, since patients with known cardiovascular disease states we not excluded from the trial the protocol appears to have evaluated the effects of krill oil on this cardiovascular risk factor while evaluating the effects of krill oil supplementation on the pain and discomfort associated with OA and RH. Group A received the NEPTUNE KRILL OIL (300 mg daily) and group B received a placebo. C-RP and Western Ontario and McMaster Universities (WOMAC) osteoarthritis scores were measured at baseline and days 7, 14 and 30. After seven days of treatment, the NEPTUNE KRILL OIL reduced CRP by 19.3% compared to an increase by 15.7% observed in the placebo group (p=0.049). After 14 and 30 days of treatment, the NEPTUNE KRILL OIL further decreased CRP by 29.7% and 30.9% respectively (p<0.001). The CRP levels of the placebo group increased to 32.1% after 14 days and then decreased to 25.1% at day 30. The between group difference was statistically significant; p=0.004 at day 14 and p=0.008 at day 30. The application of the processed NEPTUNE KRILL OIL showed a significant reduction in all three WOMAC scores. After seven days of treatment, the NEPTUNE KRILL OIL reduced pain scores by 28.9% (p=0.050 ), reduced stiffness by 20.3% (p=0.001 ) and reduced functional impairment by 22.8% (p=0.008 ). The results of that study indicate that the NEPTUNE KRILL OIL at a daily dose of about 300 mg significantly inhibits inflammation, reduces arthritic symptoms within a short treatment period of 7 and 14 days and may be effective in reducing the risk of cardiovascular disease by reduction of C-RP in the patient population employed. It is desirable if further enhanced effects be accomplished using krill oil and similar compositions, especially with improving blood lipid profiles and reducing Lin oxidation.

SUMMARY OF THE INVENTION

In accordance with a non-limiting example, even more beneficial and synergistic effects for improving blood lipid profiles and reducing LOL have been found when krill oil and/or marine oil is used in combination with astaxanthin or an LDL per-oxidation blocker, or when a mixture of fish oil derived, choline based, phospholipd bound omega-3 fatty acid mixture including phospholipid bound polyunsaturated EPA and DHA is used instead of krill oil.

The composition and method, in accordance with a non-limiting example, improves blood lipid profiles and reduces low density lipoprotein (LDL) oxidation in humans by administering a therapeutic amount of a composition comprising krill oil in combination with astaxanthin or in another embodiment, an LDL per-oxidation blocker in an oral dosage form. In one embodiment, the krill oil is derived from *Euphasia* spp ., comprising Eicosapentaenoic (EPA) and Docosahexaenoic (DHA) fatty acids in the form of triacylglycerides and phospholipids. The krill oil includes at least 10% EPA and 5% DHA, of which greater than 50% are in the form of phospholipids and the 1-4000 mg of krill oil per daily dose is delivered.

In another example, the LDL per-oxidation blocker comprises astaxanthin. In an example, 0.1-12 mg astaxanthin is supplemented to the krill oil per daily dose. The astaxanthin is derived from *Haematococcus pluvialis* algae, *Pfaffia*, krill, or by synthetic routes, in the known free diol, monoester or diester forms. In another example, the composition additionally includes a plant based, triacylglycerides bound, n-3 (omega-3) fatty acid rich oil derived from flax seed oil, perilla seed oil or chia seed oil wherein the n-3 fatty acid comprises principally alpha-linolenic acid.

In yet another example, a method and composition is disclosed that improves blood lipid profiles and reduces low density lipoprotein (LDL) oxidation in humans by administering a composition comprising a therapeutic amount of a mixture of fish oil derived choline based, phospholipid bound omega-3 fatty acid mixture including phospholipid bound polyunsaturated Eicosapentaenoic (EPA) and Docosahexaenoic (DHA). The fish oil derived, choline based, phospholipid bound fatty acid mixture includes polyunsaturated EPA and DHA and comprises Eicosapentaenoic (EPA) and Docosahexaenoic (DHA) fatty acids in the form of triacylglycerides and phospholipids. The omega choline comprises not less than (n.l.t.) 15 g/100 g of marine phospholipids, n.l.t. 12 g/100 g of DHA, and n.l.t. 7 g/100 g EPA in one example. The omega choline comprises n.l.t. 22 g/100 g of Omega-3 and less than 3 g/100 g of Omega-6. In yet another example, the composition of fish oil derived, choline based, phospholipid bound fatty acid mixture can be enriched in the phospholipid fraction by the use of supercritical solvent extraction of triacylglycerides from the phospholipid fraction to decrease the triacylglyceride based fish oil diluents and increase the fish oil derived phospholipids.

Astaxanthin may also be added to the composition fish oil derived, choline based,phospholipid bound fatty acid mixture including polyunsaturated EPA and DHA per daily dose. About 0.1-20 mg of astaxanthin are added to the fish oil derived, choline based, phospholipid bound fatty acid mixture including polyunsaturated EPA and DHA per daily dose. The astaxanthin may be derived from *Haematococcus pluvialis* algae, *Pfaffia*, krill, or by synthetic routes, in the free dial, monoester or diester forms.

DETAILED DESCRIPTION OF THE PREFERRED EMBODIMENTS

The present invention will now be described more fully hereinafter in which preferred embodiments of the invention are described. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In an embodiment using krill oil, the composition includes EPA and DHA functionalized as marine phospholipids and acyltriglycerides derived from krill, and in one example, includes esterified astaxanthin in an oral dosage form. It has been found that a new and potentially quite important biomarker for cardiovascular risk is related to the amount of EPA and DHA found in red blood cells divided by the total fatty acid content in red blood cells or the so called "omega-3 index." The compositions, in accordance with a non-limiting example, improve the omega-3 index in man on prolonged administration and therefore are presumed to lower cardiovascular event risks. Some of these components are explained in the following chart:

| Components | Percentage (%) |
|---|---|
| PHOSPHOLIPIDS<br>PC, PE, PI, PS, SM, CL | >40 |
| OMEGA-3 (functionalized on PL) | >30 |
| Eicosapentaenoid Acid (EPA) * | >17 (15% in one example and 10% in another) |
| Docosahexaenoid Acid (DHA) + | >11 (9% in one example and 5% in another) |
| ANTIOXIDANTS | (mg/100 g) |
| Astaxanthin, Vitamin A, Vitamin E | >1.25 |

\* >55% of PL-EPA/Total EPA
+ >55% of PL-DHA/Total DHA
These amounts can vary depending on application and persons.

Krill oil can be supplemented with astaxanthin to improve formulated product utility. In one study, 4 mg of astaxanthin per day for two weeks resulted in a 26% reduction of LDL cholesterol oxidation. 4 mg of astaxanthin for eight weeks resulted in a 21% decrease in C-reactive protein scores. 3.6 mg of astaxanthin per day for two weeks demonstrated that astaxanthin protects LDL cholesterol against induced in vitro oxidation.

Astaxanthin is also known to reduce C-Reactive Protein (C-RP) blood levels in vivo. For example, in human subjects with high risk levels of C-RP three months of astaxanthin treatment resulted in 43% drop in the patient population's serum C-RP levels a drop which is below the unacceptable cardiovascular event risk level. Astaxanthin is so powerful that it has been shown to negate the pro-oxidant activity of Vioxx in vitro, a COX-2 inhibitor belonging to the NSAIDS drug class which is known to cause cellular membrane lipid per-oxidation leading to heart attacks and strokes. For this reason Vioxx was subsequently removed from the US market by the FDA. Astaxanthin is also absorbed in vitro by lens epithelial cells where it suppresses UVB induced lipid per-oxidative mediated cell damage at umol/L concentrations. Reduction of C-Reactive protein (CRP), reduction of LDL oxidation and an increase in the omega-3 index in vivo would presumably all be important positive contributors to cardiovascular health since each are well know biomarkers for cardiovascular health risk. These results have been shown in:

1) Lee et al., Molecules and Cells, 16(1):97-105; 2003;
2) Ohgami et al., Investigative Ophthalmology and Visual Science 44(6):2694-2701, 2003;
3) Spiller et al., J. of the Amer. College of Nutrition, 21(5): October 2002; and
4) Harris, Pharmacol. Res. 2007 March; 55(3) 217-223.

A preferred composition in one embodiment includes 300-500 mg of krill oil and 2 mg astaxanthin.

As noted before, krill oil is typically produced from Antarctic krill (*euphausia superba*), which is a zooplankton (base of food chain). It is one of the most abundant marine biomass of about 500 million tons according to some estimates. Antarctic krill breeds in the pure uncontaminated deep sea waters. It is a non-exploited marine biomass and the catch per year is less than or equal to about 0.02% according to some estimates.

It is believed that Krill oil based phospholipid bound EPA and DHA uptake into cellular membranes is far more efficient than triacylglyercide bound EPA and DHA since liver conversion of triacylglycerides is itself inefficient and because phospholipid bound EPA and DHA can be transported into the blood stream via the lymphatic system, thus, avoiding liver breakdown. In addition, krill oil consumption does not produce the burp-back observed with fish oil based products. Because of this burp-back feature of fish oils, it has been found that approximately 50% of all consumers who try fish oil never buy it again.

Astaxanthin has an excellent safety record. A conducted study obtained the results as follows:
  Oral LID 50: 600 mg/kg (rats);
  NOAEL: 465 mg/kg (rats); or
  Serum Pharmacokinetics: Stewart et al. 2008
    1) $T_{1/2}$: 16 hours;
    2) $T_{max}$: 8 hours;
    3) $C_{max}$: 65 µg/L.

At eight weeks of supplementation at 6 mg per day, there was no negative effect in healthy adults. Spiller et al. 2003.

In accordance with one non-limiting example, astaxanthin has three prime sources. 3 mg astaxanthin per 240 g serving of non-farmed raised salmon or a 1% to 12% astaxanthin oleoresin or 1.5-2.5% beadlet derived from microalgae. Literature references pertinent to the above discussion can be found in Lee et al., Molecules and Cells 16(1): 97-105, 2003; Ohgami et al., Investigative Ophthalmology and Visual Science 44(6): 2694-2701, 2003; Spiller et al., J. of the American College of Nutrition 21(5): October 2002; and Fry et al., University of Memphis, Human Performance Laboratories, 2001 and 2004, Reports 1 and 2.

Although many beneficial and synergistic effects are now being reported herein have been observed when krill oil is used in combination with other active ingredients, and more specifically in one example, krill oil in combination with astaxanthin. It should be understood that different proportions of ingredients and percentages in compositions can be used depending on end use applications and other environmental and physiological factors when treating a patient condition.

The krill oil in one example is derived from *Euphasia* spp., comprising Eicosapentaenoic (EPA) and Docosahexaenoic (DHA) fatty acids in the form of triacylglycerides and phospholipids, although not less than 1% EPA and 5% DHA has been found advantageous. In another example, the krill oil includes at least 15% EPA and 9% DHA, of which not less than 45% are in the form of phospholipids, and in one example, greater than 50%. The composition can be delivered advantageously for therapeutic results with 1-4000 mg of krill oil delivered per daily dose. In another example, 0.1-50 mg astaxanthin are supplemented to the krill oil per daily dose, and in one example, 0.1-12 mg of astaxanthin.

The astaxanthin is preferably derived from *Haematococcus pluvialis* algae, *Pfaffia*, krill, or by synthetic routes, in the known free diol, monoester or diester form, and in one example, at a daily dose of 0.5-8 mg.

The composition may also include an n-3 (omega-3) fatty acid rich oil derived from fish oil, algae oil, flax seed oil, or chia seed oil when the n-3 fatty acid comprises alpha-linolenic, stearidonic, eicosapentaenoic or docosapentaenoic acid. The composition may include naturally-derived and synthetic antioxidants that are added to retard degradation of fatty acids and astaxanthin.

Details of a type of CO2 extraction and processing technology (as supercritical CO2 extraction) and peroxidation blocker technology that can be used are disclosed in commonly assigned U.S. Patent Publication Nos. 2009/0181127; 2009/0181114; and 2009/0258081, the disclosures which are hereby incorporated by reference in their entirety.

As noted before, there are beneficial aspects of using krill oil in synergistic combination with other ingredients. It has been determined that a fish oil derived, choline based, phospholipid bound omega-3 fatty acid mixture including phospholipid bound polyunsaturated EPA and DHA is also advantageous for improving blood lipid profiles and reducing LDL either alone or admixed with other ingredients, for example, an LDL per-oxidation blocker. One commercially available example of a mixture of fish oil derived, choline based, phospholipid bound fatty acid mixture including polyunsaturated EPA and DHA is Omega Choline 1520F as a phospholipid, omega-3 preparation, which is derived from natural fish oil and sold by Enzymotec Ltd. One example of such composition is described below:

| Ingredients (g/100 g): | |
| --- | --- |
| Pure Marine Phospholipids | n.l.t. 15 |
| DHA* | n.l.t. 12 |
| EPA** | n.l.t. 7 |
| Omega-3 | n.l.t. 22 |
| Omega-6 | <3 |
| Analytical Data: | |
| Peroxide value (meq/Kg) | n.m.t. 5 |
| Loss on Drying (g/100 g) | n.m.t. 2 |
| Physical Properties: | |
| Consistency | Viscous Liquid |

*Docosahexaenoic acid
**Eicosapenteanoic acid

In accordance with a non-limiting example, the method improves blood lipid profiles and either alone or in combination with added astaxanthin, such as a per-oxidation blocker, and reduces LDL oxidation in a patient by administering a therapeutic amount of a composition including a mixture of fish oil derived, choline based, phospholipid bound omega-3 fatty acid mixture including phospholipid bound polyunsaturated EPA and DHA either alone or admixed with an LDL per-oxidation blocker such as astaxanthin. In one example, the composition is supplemented in combination with astaxanthin in an oral dosage form. The mixture of fish oil derived, choline based, phospholipid bound fatty acid mixture including polyunsaturated EPA and DHA in one example comprises Eicosapentaenoic (EPA) and Docosahexaenoic (DHA) fatty acids in the form of triacylglycerides and phospholipids. In another example, the omega choline includes at least 7% EPA and 12% DHA, of which not less than 15% are in the form of phospholipids. The composition can be delivered advantageously for therapeutic results with 1-4000 mg of a mixture of fish oil and fish oil derived, choline based, phospholipid bound fatty acid mixture including polyunsaturated EPA and DHA delivered per daily dose. In another example, 0.1-20 mg astaxanthin are supplemented to the Omega Choline per daily dose.

It should be understood that an instant formulation can be used for LDL reduction using only a mixture of fish oil derived, choline based, phospholipid bound fatty acid mixture including polyunsaturated EPA and DHA. It is also possible to use a mixture of fish oil derived, choline based, phospholipid bound omega-3 fatty acid mixture (including polyunsaturated EPA and DHA) mixed with astaxanthin. It should also be understood that an enriched version of a mixture of fish oil derived, choline based, phospholipid bound fatty acid mixture including polyunsaturated EPA and DHA can be used wherein the fraction of added fish oil diluents has been decreased and the proportion of fish oil derived phospholipids has been increased. This can be accomplished by using supercritical CO2 and/or solvent extractions for selective removal of triacylgycerides from phospholipids. The composition may also include a natural or synthetic cyclooxygenase-1 or -2 inhibitor comprising for example aspirin, acetaminophen, steroids, prednisone, or NSAIDs.

The composition may also include a gamma-linoleic acid rich oil comprising Borage (*Borago officinalis* L.) or Safflower (*Carthamus tinctorius* L.), which delivers a metabolic precursor to $PGE_1$ synthesis.

The composition may also include an n-3 (omega-3) fatty acid rich oil derived from fish oil, algae oil, flax seed oil, chia seed oil or perilla seed oil wherein the n-3 fatty acid source comprises alpha-linolenic, stearidonic, eicosapentaenoic or docosapentaenoic acid. The composition may include naturally-derived and synthetic antioxidants that are added to retard degradation of fatty acids such as tocopherols, tocotrienols, carnosic acid or Carnosol and/or astaxanthin.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method to treat low density lipoprotein (LDL) oxidation in humans by administering a therapeutic amount of a dietary supplement composition comprising krill oil in combination with astaxanthin derived from *Haematococcus pluvialis* (Hp) in an oral dosage form, wherein the astaxanthin derived from *Haematococcus pluvialis* (Hp) is 0.4 to 0.67 percent by weight of the krill oil.

2. The method according to claim 1, wherein the krill oil is derived from *Euphasia* spp., comprising Eicosapentaenoic (EPA) and Docosahexaenoic (DHA) fatty acids in the form of triacylglycerides and phospholipids.

3. The method according to claim 2, wherein the krill oil includes at least 10% EPA and 5% DHA.

4. The method according to claim 1, further comprising delivering 1-4000 mg of krill oil per daily dose.

5. The method according to claim 1, further comprising delivering krill oil supplemented with 0.1-12 mg astaxanthin per daily dose.

6. The method according to claim 1, wherein the astaxanthin is derived from *Haematococcus pluvialis* algae oleoresin or beadlet.

7. The method according to claim 1, wherein the composition includes an n-3 (omega-3) fatty acid rich oil derived from flax seed oil, perilla seed oil, or chia seed oil, wherein the n-3 fatty acid comprises alpha-linolenic acid.

* * * * *

UNITED STATES PATENT AND TRADEMARK OFFICE
CERTIFICATE OF CORRECTION

PATENT NO.       : 8,663,704 B2                                    Page 1 of 1
APPLICATION NO.  : 13/093201
DATED            : March 4, 2014
INVENTOR(S)      : Minatelli et al.

It is certified that error appears in the above-identified patent and that said Letters Patent is hereby corrected as shown below:

In the Specification

Column 2, Line 37       Delete:
                          "reducing Lin oxidation."

Insert:
                          -- reducing LDL oxidation. --

Signed and Sealed this
Third Day of June, 2014

Michelle K. Lee
*Deputy Director of the United States Patent and Trademark Office*